Figure 1:
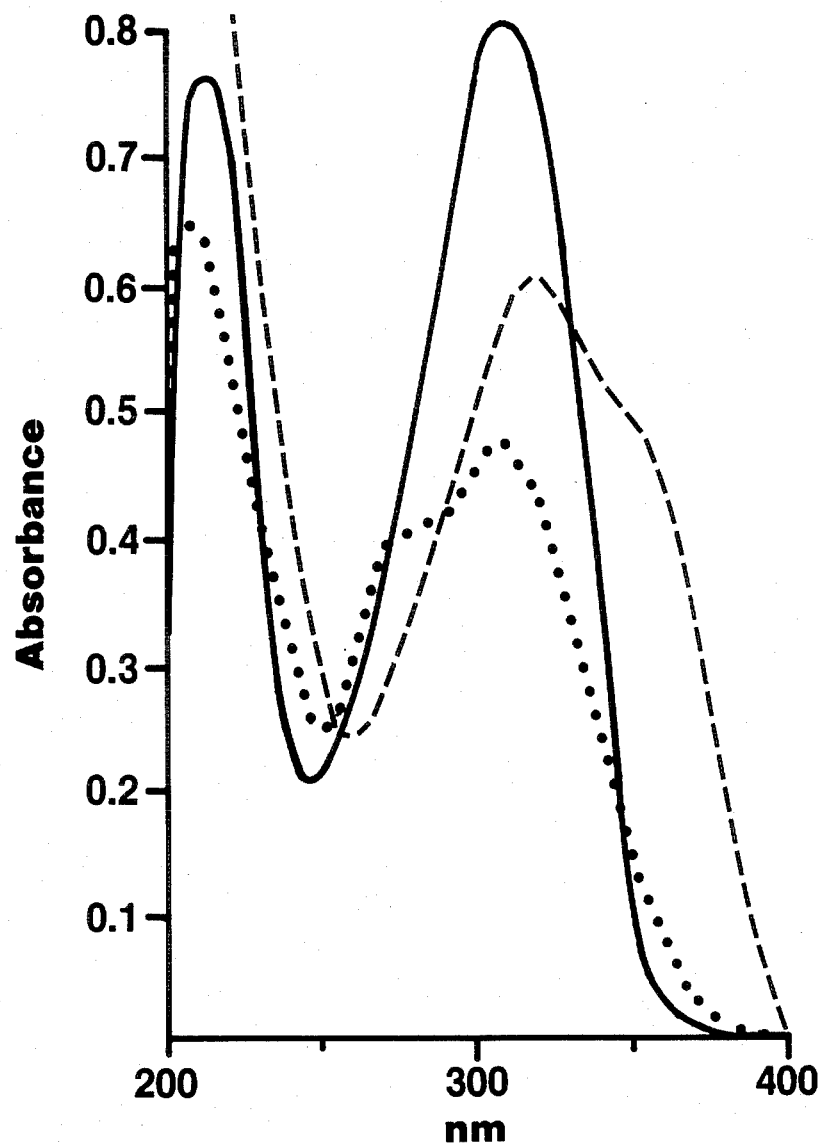
Figure 2:
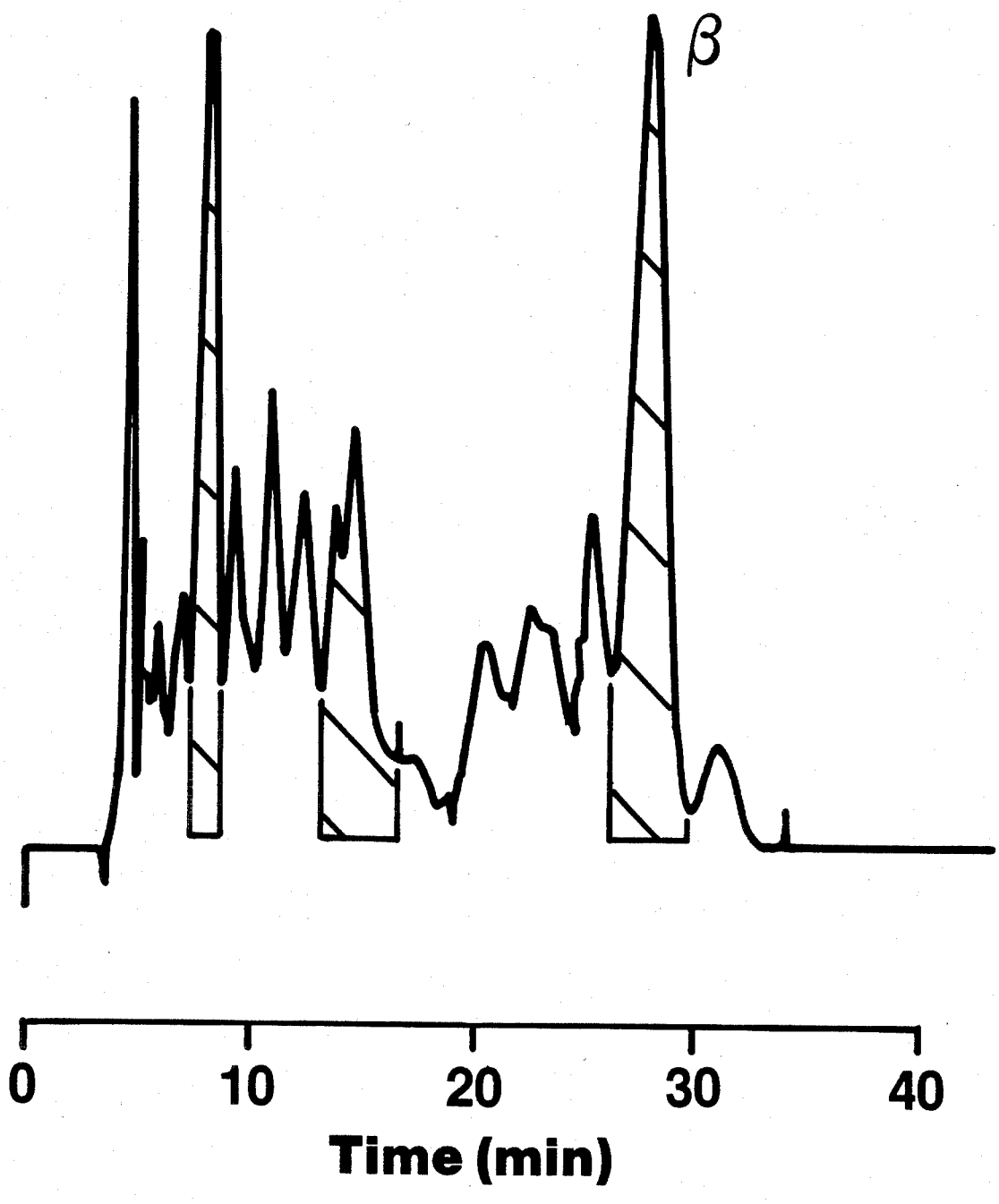
Figure 3:
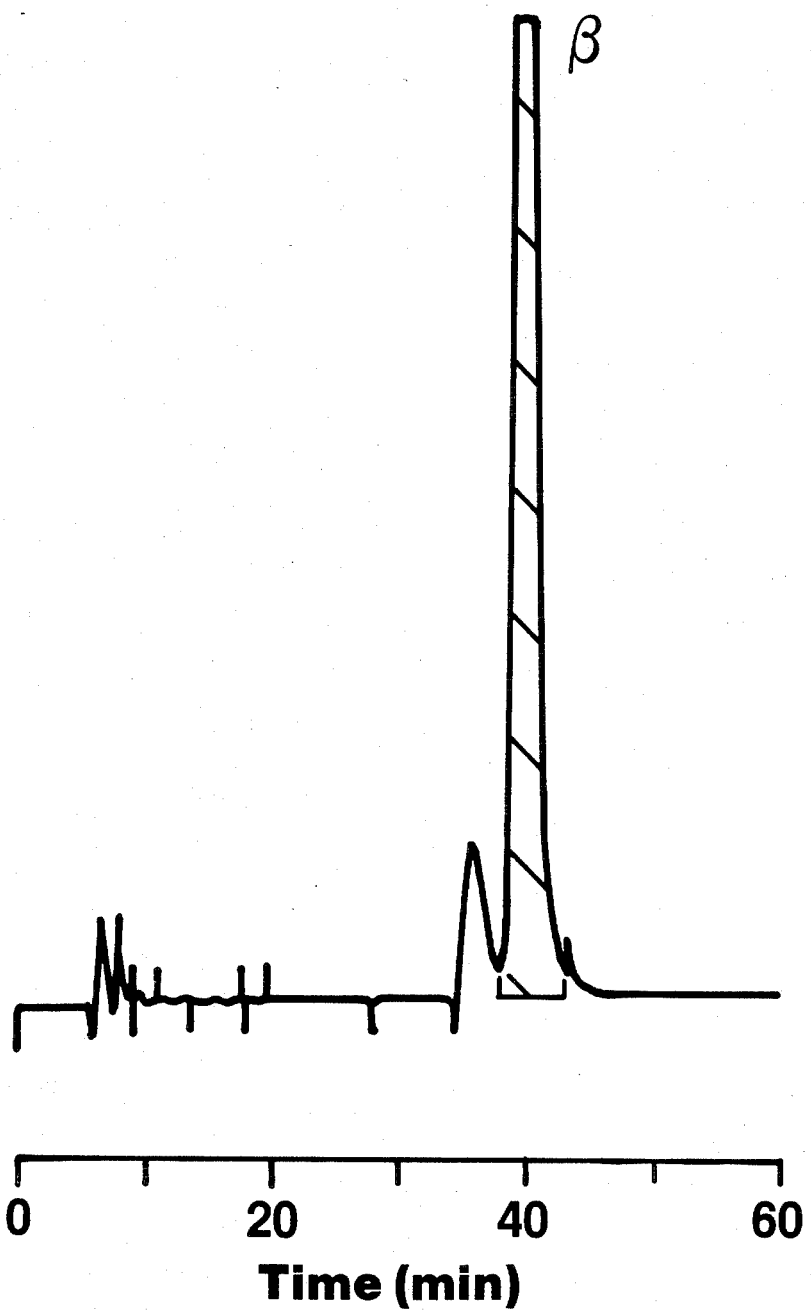

| United States Patent [19] | [11] Patent Number: 4,525,354 |
| Birch et al. | [45] Date of Patent: Jun. 25, 1985 |

[54] ANTIBIOTIC AND PROCESS FOR THE PRODUCTION THEREOF

[75] Inventors: Robert G. Birch, Brighton, Australia; Suresh S. Patil, Honolulu, Hi.

[73] Assignee: University of Hawaii, Honolulu, Hi.

[21] Appl. No.: 531,879

[22] Filed: Sep. 14, 1983

[51] Int. Cl.³ .......................... A61K 35/74; C12P 1/04; C12P 1/02

[52] U.S. Cl. .................................. 424/115; 435/170; 435/171

[58] Field of Search ................. 424/115; 435/171, 170

Primary Examiner—Jerome D. Goldberg
Attorney, Agent, or Firm—William B. Scanlon; Arthur R. Whale

[57] ABSTRACT

Antibiotic albicidin, a non-peptide antibiotic, is produced by culturing chlorosis-inducing strains of *Xanthomonas albilineans* isolated from diseased sugarcane, and mutants thereof. The antibiotic is isolated from the culture medium by adsorption on resin and is purified by gel filtration and HPLC.

3 Claims, 3 Drawing Figures

Absorption Spectra of Albicidin (10 μg/ml) in: (——) Methanol, (----) 0.06N Methanolic KOH, (•••) 0.01 M Tris-HCl Buffer pH 7.0.

ANTIBIOTIC AND PROCESS FOR THE PRODUCTION THEREOF

BACKGROUND OF THE INVENTION

This invention relates to an antibiotic substance and to a method for its production. In particular, it relates to a broad spectrum antibiotic produced by culturing *Xanthomonas albilineans* in an aqueous nutrient culture medium.

During our study of leaf scald disease of sugarcane (*Saccharum officinarum* L.) caused by the xylem-invading bacterium *Xanthomonas albilineans* (Ashby) Dowson, it appeared likely that the organism may produce a diffusible phytotoxin. We cultured chlorosis-inducing *X. albilineans* (Ashby) Dowson strain LS2, an original isolate from diseased sugarcane from Hawaii, in attempting to demonstrate a phytotoxin. Although the production of antimicrobial agents by the genus Xanthomonas has not been previously reported, we were able to isolate a mixture of antibiotic substances and to isolate and purify the major antibacterial component of the mixture. This antibiotic, which we have designated by the arbitrary name albicidin, has been found to inhibit the growth of a broad spectrum of microorganisms pathogenic to man and animals.

SUMMARY

The broad spectrum antibiotic albicidin is produced by culturing chlorosis-inducing strains of *Xanthomonas albilineans* in aqueous nutrient culture media until a substantial amount of antibiotic activity is produced. Preferably, the culture is grown to the stationary phase for maximum antibiotic production. Cells are separated from the antibiotic containing medium, the antibiotic adsorbed on an acrylic ester polymeric absorbant resin and eluted with methyl alcohol. The antibiotic eluate is concentrated, diluted with acetone and stored in the cold to precipitate inactive material. The inactive material is separated and the antibiotic-containing liquid phase is further purified by gel filtration and high performance liquid chromatography. Albicidin is isolated as a white crystalline compound.

DESCRIPTION OF THE DRAWINGS

FIG. 1 is the ultraviolet absorption spectra of albicidin in methanol, in methanolic KOH, and in water pH 7.

FIG. 2 is the HPLC elution profile of albicidin from a Hamilton PRP-1 column.

FIG. 3 is the HPLC elution profile for albicidin from a Beckman ODS column.

DETAILED DESCRIPTION

Albicidin, provided by this invention, is a non-peptide antibiotic obtained as a white crystalline compound soluble in polar organic solvents such as, methyl alcohol, ethyl alcohol, tetrahydrofuran, dimethylacetamide, dimethylformamide, 95% acetone, and dimethylsulfoxide. It is sparingly soluble in water and acetonitrile and is essentially insoluble in less polar solvents.

Albicidin absorbs radiation in the ultraviolet region of the spectrum. The ultraviolet absorption spectrum of albicidin is shown in FIG. 1 of the drawings. In methanol (10 mcg/ml) the spectrum shows absorption maxima at λmax 213 nm and λmax 308 nm, $E_{1\,cm}^{1\%}=8\times10^2$. The addition of potassium hydroxide to 0.06N in the methanol solution shifted the maximum at 308 nm to 320 nm with a shoulder near 350 nm. In aqueous solution at pH 7 (0.01M Tris-HCl buffer) the spectrum shows λmax at 308 nm with a shoulder at 275 nm.

The proton magnetic resonance spectrum for albicidin is as follows:

$^1$HNMR (DMSO-$d_6$, 300 MHz); δ11.567 (1H, br s), 11.178 (1H, s), 10.597 (1H, s), 10.131 (1H, s), 9.802 (1H, br s), 9.719 (1H, s), 9.042 (1H, d, J=7.8 Hz), 8.039 (1H, d, J=8.8 Hz), 8.009 (1H, d, J=8.8 Hz), 7.939 (1H, d, J=8.9 Hz), 7.870 (1H, d, J=8.9 Hz), 7.828 (1H, d, J=8.8 Hz), 7.811 (1H, d, J=8.8 Hz), 7.600 (1H, br d, J=8.8 Hz), 7.372 (2H, d, J=8.8 Hz), 7.287 (1H, br q, J=1.2 Hz), 6.858 (2H, d, J=8.8 Hz), 5.003 (1H, br td, J=8.5, 7.8, and 5.6 Hz), 3.931 (3H, s), 3.795 (3H, s), 3.165 (1H, dd, J=−16.9 and 5.6 Hz), 3.097 (1H, dd, J=−16.9 and 8.5 Hz), 2.136 (3H, d, J=1.2 Hz).

The carbon $^{13}$NMR spectrum obtained with albicidin is as follows: (each signal is that of a single carbon unless otherwise indicated)

$^{13}$C NMR (DMSO-$d_6$, 75 MHz): δ168.89 (s), 168.19 (s), 166.17 (s), 164.86 (s), 163.30 (s), 157.52 (s), 154.49 (s), 149.72 (s), 142.70 (s), 141.86 (s), 140.26 (s), 137.76 (s), 136.15 (s), 135.90 (s), 133.92 (d), 131.31 (d, 2C), 129.51 (s), 128.99 (s), 128.80 (d), 128.36 (d), 127.65 (s), 126.55 (s), 125.70 (d), 125.48 (d), 119.14 (d), 118.95 (d), 118.22 (s), 116.25 (s), 115.39 (d, 2C), 114.94 (d), 110.20 (d), 60.56 (q), 60.22 (q), 50.62 (d), 20.03 (t), 14.57 (q).

The molecular weight of albicidin is 842 as determined by mass spectrometry. The fast atom bombardment (FAB) mass spectrum gave $(M+H)^+$ of 843, while the field desorption mass spectrum (FDMS) gave $(M+H)^+$ of 843 and M/Z 799 (843-44) indicating the loss of a carboxylate group.

Albicidin is relatively stabile at low pH but relatively unstabile at high pH, as indicated by its retention or loss of antibacterial activity. For example, when an aqueous solution of albicidin was maintained at a temperature of 100° C. for 30 minutes, activity was undiminished. After 3 hours at 25° C. at pH 1.0, activity was undiminished; however, after 3 hours at 25° C. at pH 10.0, activity was eliminated.

Albicidin activity was undiminished after 3 hours at 37° C. in the presence of the non-specific proteolytic enzyme pronase at a concentration of 50 mcg/ml.

Albicidin is best stored as a dry powder; however, solutions of the antibiotic in methyl alcohol were stored at −20° C. for up to 6 months without loss of activity.

Albicidin is produced by culturing under aerobic conditions a chlorosis-inducing strain of *Xanthomonas albilineans* or a chlorosis-inducing mutant thereof in an aqueous nutrient culture medium until a substantial amount of antibiotic activity is produced.

The microorganism employed in the production of albicidin is a known pathogen of the sugarcane plant, *Saccharum officinarum* L. *X. albilineans* is the causative agent of the common leaf scald disease of sugarcane. The pathogen invades the xylem of the plant and disease symptoms include the emergence of leaves with narrow, sharply defined white stripes, referred to as "white pencil lines", parallel to the main veins on leaves and leaf sheaths. As the stripes age a diffuse chlorotic zone often develops around the sharply defined central white lines. Partial or complete white chlorosis of emerging leaves may occur as the disease progresses, and is not restricted to leaves with narrow pencil lines. The pathogen can be isolated from leaf pencil lines and stalk tissue showing internal red streaks, but not from chlorotic tissue away from the pencil lines.

We have found that naturally occurring strains of *X. albilineans* and mutants thereof that induce chlorosis in sugarcane plants also produce albicidin when cultured in aqueous nutrient media.

In one of its aspects, this invention provides a process for producing albicidin which comprises culturing a chlorosis-inducing strain of *X. albilineans* or mutants thereof under aerobic conditions in an aqueous nutrient culture medium until a substantial amount of antibiotic activity is produced.

Isolates of *X. albilineans* were obtained as described by Persley from stalk and leaf tissue of sugarcane varieties showing characteristic symptoms of leaf scald disease (Persley, G. J., 1972, "Isolation Methods for the Causal Agent of Leaf Scald Disease", *Sugarcane Pathologists' Newsletter,* 8:24.) Bacteriological characterization of these Hawaiian isolates has been described, Birch, R. G., 1980, "Investigation of the Role of a Phytotoxin in the Pathogenicity of *Xanthomonas albilineans,* Causing Leaf Scald Disease of Sugarcane", M.S. Thesis, University of Hawaii, 163 pages.

This invention further provides a process for the production of albicidin which comprises culturing *X. albilineans* LS20, NRRL B-15550 in an aqueous nutrient culture medium until a substantial amount of antibiotic is produced. *X. albilineans* LS20, NRRL B-15550 is a mutant obtained with the known natural strain *X. albilineans* LS2 by nitrosoguanidine mutagenesis. The LS20 mutant is a preferred strain of the organism of this invention since higher yields of albicidin of about four times those generally obtained with the known LS2 strain are produced with the mutant.

The mutant strain *X. albilineans* LS20 has been deposited without restriction as to public availability in the permanent culture collection of the Fermentation Laboratory, Northern Regional Research Center, U.S. Dept. of Agriculture, 1815 North University Street, Peoria, Ill. 61604, where it has been assigned the accession number NRRL B-15550.

*Xanthomonas albilineans* strain LS2 is an original isolate from diseased sugarcane from Hawaii. We have characterized the LS2 isolate in bacteriological tests, and it is typical of the species described in *Bergey's Manual of Determinative Bacteriology,* 8th Ed., Buchanan, R. E. & Gibbons, N. E., ed., The Williams & Wilkins Company, Baltimore, at pages 244–245. The LS2 strain is typical of natural disease-causing isolates.

The chlorosis-inducing strains of *X. albilineans* can be cultured in a variety of nutrient media. The medium in general contains sources of carbon, nitrogen, and inorganic salts. Sources of carbon which can be utilized are the sugars such as sucrose, glucose, mannose, and galactose. Starches may also be used. Sources of nitrogen include the amino acids, in particular methionine, glutamic acid, protein hydrolysates, peptones, ammonium ion, and the like. As with the growth of most microorganisms, sources of inorganic cations and anions are needed and often have a beneficial effect on the growth. Sources for such ions typically include the inorganic salts such as potassium chloride, ammonium chloride, sodium sulfate, magnesium sulfate, potassium phosphate, potassium hydrogen phosphate, magnesium sulfate, and like salts. In addition, minor amounts of trace elements may produce a beneficial effect on the growth of the bacteria and the production of albicidin. Such trace elements usually are added as trace impurities in other ingredients employed in the media.

A preferred medium for the production of albicidin is sucrose-peptone medium (SP) adjusted to pH 7 and having the following composition:

| Ingredient | g/l |
|---|---|
| Sucrose | 20 |
| Peptone | 5 |
| Dipotassium Phosphate | 0.5 |
| Magnesium Sulfate Heptahydrate | 0.25 |

The organism can be grown at a temperature between about 15° C. and about 37° C.; however, the best growth and the best yields of albicidin are obtained at a temperature between about 28° C. to about 30° C.

Maximum production of albicidin occurs early in the stationary phase with cultures grown at the preferred temperature of 28° C. to 30° C.

The fermentation can be carried out on a small scale in shake flasks, for example, in Fernback flasks or in Erlenmeyer flasks. The flasks are shaken or oscillated during the fermentation. For large-scale production of the antibiotic, sterile, stainless steel fermentation tanks equipped with a stirrer and aeration tube are used.

The fermentation is carried out for about 80 hours to about 150 hours with maximum antibiotic production occurring at about 90 to about 110 hours. The fermentation can be monitored for antibiotic production by withdrawing an aliquot of medium for assay of antibiotic content. The assay organism we used is *Escherichia coli* UHP1, a prototrophic, wild-type strain obtained from the Department of Microbiology, University of Hawaii. Other strains of *E. coli* may be used. Since *X. albilineans* produces valine during the fermentation, the *E. coli* strain should not be inhibited by valine. Other microorganisms such as *Bacillus subtilis* may be employed for assay purposes.

For quantitative assays of inhibitory activity, 10 ml basal layers of glucose minimal A agar (Example 1) were poured in 9 cm Petri dishes and allowed to dry for 48 hours at 25° C. Plates were then overlaid with a mixture of 2 ml log-phase *E. coli* UHP1 at $2\times10^7$ cells/ml in glucose minimal A medium, plus 2 ml molten 2% Difco Noble agar at 65° C. Serial dilutions of test preparations were assayed by adding 20 μl volumes to 5 mm diameter wells cut in the overlaid plates. Inhibition zone width was recorded after 12 hours incubation at 37° C. The quantity of antibiotic causing an inhibition zone of 3 mm width was arbitrarily designated as one activity unit. The minimum inhibitory concentration (MIC) in liquid culture corresponds approximately to 1 unit/20 μl in the plate assay. Standard preparations were included in comparative quantitative assays, because the slope of the dose-response line varies with slight changes in assay conditions.

After the fermentation is terminated, the bacterial cells are separated from the antibiotic medium and the antibiotic recovered from the medium by adsorption on a chromatographic resin. The cells are best separated from the culture medium by centrifugation, although they may be separated by filtration on a suitable filter material. No detectable antibiotic activity is recovered from the separated and washed cells after sonication.

The antibiotic is recovered from the cell-free medium by adsorption on a chromatographic resin such as a polymeric acrylic ester adsorbant of intermediate polarity. One such resin which can be used is Amberlite XAD-7 or XAD-8 (Rohm and Haas). The antibiotic is eluted from the resin with a lower alcohol, preferably methanol, and the eluate is concentrated by evaporation of the eluant. The aqueous antibiotic concentrate is diluted with acetone to 95% v:v acetone and is stored in the cold (about 5° C.). The precipitate of inactive impurities of high molecular weight is separated and the liquid phase is evaporated to remove the acetone. The concentrate is diluted with methyl alcohol or other solvent and further purified by gel filtration and reverse phase high performance liquid chromatography (HPLC). The gel filtration can be carried out in a suitable gel such as Sephadex LH-20 (Pharmacia Fine Chemicals). Antibiotic activity is recovered as a single peak from the LH-20 gel filtration.

The gel filtration is followed by further purification (single peak off LH-20) via reverse phase HPLC on a macroreticular resin column, for example, on a Hamilton PRP-1 column. Albicidin of the best purity is obtained by a further reverse phase HPLC on octadecylsilane, for example, on a Beckman ODS column. The reverse phase HPLC is best carried out using isocratic elution with 44% v/v tetrahydrofuran in water containing 1% v/v acetic acid.

Albicidin is the major component of the antibacterial components resolved by HPLC and comprises about 80% of total activity. The albicidin was recovered from the HPLC eluate by allowing tetrahydrofuran to evaporate slowly from the pooled fractions in the active peak and collecting the white crystalline albicidin by filtration.

The crystalline albicidin appeared chromatographically pure on analytical octadecylsilane, cyano and phenyl bonded-phase HPLC columns.

Albicidin inhibits the growth of microorganisms pathogenic to man and animals. The following Table 1 shows the in vitro activity of albicidin against representative strains of gram-positive and gram-negative organisms as determined by the agar dilution method.

TABLE 1
IN VITRO ACTIVITY OF ALBICIDIN

| Test Organism | Strain | Mic (μg/ml)[1] |
|---|---|---|
| *Staphylococcus aureus* | X1.1 | 1.6 |
| " | V41 | 0.4 |
| " | X400 | 25+ |
| " | S13E | 0.4 |
| *Staphylococcus epidermidus* | EPI1 | 1.6 |
| " | 222 | 25+ |
| *Streptococcus pyogenes* | C203 | 0.8 |
| *Streptococcus pneumoniae* | Park | 25+ |
| *Streptococcus* Group D | X66 | 25+ |
| " | 2041 | 25+ |
| *Haemophilus influenzae* | C.L | 0.05 |
| " | 76 | −0.001 |
| *Escherichia coli* | N10 | 0.05 |
| " | EC14 | 0.1 |
| " | TEM | 0.012 |
| *Klebsiella pneumoniae* | X26 | 25+ |
| " | KAE | 0.2 |
| " | X68 | 25+ |
| *Enterobacter aerogenes* | C32 | 25+ |
| " | EB17 | 0.1 |
| *Enterobacter cloacae* | EB5 | 25+ |
| " | 265A | 25+ |
| *Salmonella typhi* | X514 | 0.8 |
| " | 1335 | 0.2 |
| *Pseudomonas aeruginosa* | X528 | 1.6 |
| " | X239 | 25+ |
| " | PS18 | 25+ |
| " | PS72 | 1.6 |
| *Serratia marcescens* | X99 | 25+ |

TABLE 1-continued
IN VITRO ACTIVITY OF ALBICIDIN

| Test Organism | Strain | Mic (μg/ml)[1] |
|---|---|---|
| " | SE3 | 25+ |
| *Shigella sonnei* | N9 | 0.012 |
| *Proteus morganii* | PR15 | 0.2 |
| *Proteus inconstans* | PR33 | 25+ |
| *Proteus rettgeri* | C24 | 25+ |
| *Citrobacter freundii* | CF17 | 25+ |
| *Acinetobacter calcoaceticus* | AC12 | 25+ |

[1]A + sign means greater than, while the − sign means less than.

Albicidin can be formulated into antiseptic compositions suitable for topical use. Liquid compositions comprising albicidin at a concentration between about 1% and about 20% can be prepared in a suitable polar organic solvent or mixtures thereof. For example, solutions of the antibiotic can be made up in methyl alcohol or ethyl alcohol and dimethylsulfoxide. The solutions also may contain stabilizers, antioxidants, solubilizing agents, and buffers. The albicidin compositions may be applied to the skin to control or prevent infections of cuts, abrasions, lacerations, rashes, and burns.

The following Examples further illustrate and describe the present invention.

EXAMPLE 1

Isolation of *Xanthomonas albilineans* from sugarcane

Isolates of *X. albilineans* were obtained as described by Persley supra from stalk and leaf tissues of sugarcane varieties H58-8029 and H60-6314 showing characteristic symptoms of leaf scald disease. Sucrose peptone medium and minimal medium were solidified when necessary with 1.5% Difco Bacto agar. The sucrose peptone medium was of the composition described hereinabove, while the minimal medium was of the following composition:

| Ingredient | g/l |
|---|---|
| Sucrose | 5 to 20 |
| L-Methionine | 0.1 |
| $K_2HPO_4$ | 3 |
| $NaH_2PO_4$ | 1 |
| $NH_4Cl$ | 1 |
| $MgSO_4.7H_2O$ | 0.3 |

Cells of each strain were spotted onto plates of sucrose peptone agar using sterile toothpicks, and the inoculated plates were incubated at 28° C. for 5 days. Plates were then overlaid with a mixture of 2 ml log-phase *E. coli* at $2\times10^7$ cells/ml in glucose minimal A medium (Miller, J. H., 1972, *Experiments in Molecular Genetics,* Cold Spring Harbor Laboratory, Cold Spring Harbor, N.Y.) plus 2 ml of molten 2% Difco Noble agar at 65° C. The plates were examined for zones of inhibition after 12 hours at 37° C.

EXAMPLE 2

Preparation of *X. albilineans* LS20 mutant NRRL B-15550

A cell suspension of the natural isolate LS2 was treated with the mutagen N-methyl-N'-nitro-N-nitrosoguanidine (NG) at 40 μg/ml for 10 seconds at 24° C. Cells were harvested by centrifugation and washed to remove the mutagen. A 20% to 60% kill resulted. The cells were resuspended, plated, and assayed for activity against *E. coli* by overlaying the plates as described in Example 1.

EXAMPLE 3

Production of albicidin

Sucrose peptone medium, 1.5 l. contained in a 2.8 l. Fernback flask was inoculated with *X. albilineans* LS20 mutant NRRL B-15550 and the inoculated medium was incubated for 96 hours at 28° C. with shaking on a rotary shaker at 200 rpm. The cells were removed by centrifugation and the supernatant was passed over Amberlite XAD-7 resin to adsorb the antibiotic activity. The antibiotic activity was eluted from the resin with methanol, and the eluate was evaporated under vacuum to an aqueous concentrate. The concentrate was diluted with acetone to 95% v/v acetone and stored at 5° C. for 12 hours to precipitate inactive high molecular weight impurities. The filtrate was evaporated and the residue dissolved in methanol. The solution was passed through a 120×2.5 cm column packed with Sephadex LH20 (Pharmacia Fine Chemicals) at a flow rate of 1 ml/min. Antibacterial activity was recovered in a single peak at Ve=1 liter (Ve/Vo=5.0).

The material from the single active peak was chromatographed via reverse phase HPLC on a Hamilton PRP-1 column (30.5×0.7 cm), then a Beckman ODS column (25×1 cm) using, in both cases, isocratic elution with 44% v/v tetrahydrofuran in water containing 1% v/v acetic acid. The HPLC were run at 24° C. at a flow rate of 2 ml/min. Detection was in the UV at 255 nm, 2AUFS. For the PRP-1 column the sample volume was 100 μl from the LH-20 active peak, while for the ODS column the sample was 500 μl from the PRP-1 albicidin peak.

The major component, albicidin, comprising 80% of the total activity was eluted last from the ODS column at Ve=78 to 80 ml.

FIG. 2 of the drawings shows the elution profile for the PRP-1 column, while FIG. 3 shows the elution profile for the ODS column. The major active peaks are shaded and the peak labeled by "β" is the albicidin peak.

The pooled albicidin containing fractions from the ODS column were allowed to evaporate slowly to precipitate white crystalline albicidin.

EXAMPLE 4

Inoculation of sugarcane and corn with *X. albilineans* isolates and mutants

Chlorosis-inducing strains of *X. albilineans* can be identified as such by inoculating young leaf scald susceptible cultivars as follows:

Young plants of leaf scald susceptible sugarcane cultivar H54-2508 and sweet corn cultivar Hawaiian Supersweet #9 were inoculated by decapitating plants above the shoot apex and applying a dense suspension from a 3-day slant culture of *X. albilineans* strain LS2 to the freshly cut surface. Inoculated plants were maintained in the greenhouse until systemic symptoms appeared. Only sharply defined white pencil lines developed on uncut emerging leaves of Hawaiian Supersweet #9, usually 2–4 weeks after inoculation. Systemic pencil lines, and later general chlorosis of emerging leaves, appeared in H54-2508 at variable periods of 3 weeks to 6 months after inoculation.

We claim:

1. The antibiotic albicidin when produced by culturing *Xanthomonas albilineans* strain NRRL B-15550 at a temperature between 15° C. and about 37° C. in an aqueous nutrient culture medium under aerobic fermentation conditions until a substantial amount of antibiotic activity is produced, said antibiotic being a white crystalline compound sparingly soluble in water, soluble in polar organic solvents, and substantially insoluble in non-polar organic solvents; has a molecular weight of about 842; has the following proton magnetic resonance spectrum;

$^1$HNMR (DMSO-$d_6$, 300 MHz; δ11.567 (1H, br s), 11.178 (1H, s), 10.597 (1H, s), 10.131 (1H, s), 9.802 (1H, br s), 9.719 (1H, s), 9.042 (1H, d, J=7.8 Hz), 8.039 (1H, d, J=8.8 Hz), 8.009 (1H, d, J=8.8 Hz), 7.939 (1H, d, J=8.9 Hz), 7.870 (1H, d, J=8.9 Hz), 7.828 (1H, d, J=8.8 Hz), 7.811 (1H, d, J=8.8 Hz), 7.600 (1H, br d, J=8.8 Hz), 7.372 (2H, d, J=8.8 Hz), 7.287 (1H, br, q, J=1.2 Hz), 6.858 (2H, d, J=8.8 Hz), 5.003 (1H, br td, J=8.5, 7.8, and 5.6 Hz), 3.931 (3H, s), 3.795 (3H, s), 3.165 (1H, dd, J=−16.9 and 5.6 Hz), 3.097 (1H, dd, J=−16.9 and 8.5 Hz), 2.136 (3H, d, J=1.2 Hz); has the following carbon $^{13}$NMR spectrum:

$^{13}$C NMR (DMSO-$d_6$, 75 MHz): δ168.89 (s), 168.19 (s), 166.17 (s), 164.86 (s), 163.30 (s), 157.52 (s), 154.49 (s), 149.72 (s), 142.70 (s), 141.86 (s), 140.26 (s), 137.76 (s), 136.15 (s), 135.90 (s), 133.92 (d), 131.31 (d, 2C), 129.51 (s), 128.99 (s), 128.80 (d), 128.36 (d), 127.65 (s), 126.55 (s), 125.70 (d), 125.48 (d), 119.14 (d), 118.95 (d), 118.22 (s), 116.25 (s), 115.39 (d, 2C), 114.94 (d), 110.20 (d), 60.56 (q), 60.22 (q), 50.62 (d), 20.03 (t), 14.57 (q); which has the following ultraviolet absorption spectrum:

λmax 308 nm with shoulder at 275 nm in aqueous solution, pH 7, 0.01M tris-HCl buffer, λmax 213 nm and λmax 308 nm in methyl alcohol (10 mcg/ml), $E_{1\,cm}^{1\%}=8\times10^2$, λmax 320 nm with shoulder at 350 nm in 0.06N potassium hydroxide in methyl alcohol; and which is stabile for 3 hours at 37° C. to a concentration of the proteolytic enzyme pronase of about 50 μg/ml.

2. The process for producing the antibiotic of claim 1 which comprises culturing at a temperature between about 15° C. and about 37° C. *Xanthomonas albilineans* NRRL B-15550 in an aqueous nutrient culture medium under aerobic conditions until a substantial amount of antibiotic activity is produced.

3. The process of claim 2 wherein the culture of *Xanthomonas albilineans* is grown to the stationary phase.

* * * * *